US007210353B2

(12) United States Patent
Braun et al.

(10) Patent No.: US 7,210,353 B2
(45) Date of Patent: *May 1, 2007

(54) MULTIMEDIA FEATURE FOR DIAGNOSTIC INSTRUMENTATION

(75) Inventors: Leroy Braun, Austin, TX (US); Jack Foreman, Pflugerville, TX (US)

(73) Assignee: Diagnostic Group, LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/685,240

(22) Filed: Oct. 14, 2003

(65) Prior Publication Data

US 2004/0074304 A1  Apr. 22, 2004

Related U.S. Application Data

(60) Continuation of application No. 10/156,415, filed on May 28, 2002, now Pat. No. 6,644,120, which is a division of application No. 09/139,858, filed on Aug. 25, 1998, now Pat. No. 6,416,482, which is a continuation of application No. 08/639,694, filed on Apr. 29, 1996, now Pat. No. 5,811,681.

(51) Int. Cl.
*A61B 5/12* (2006.01)
(52) U.S. Cl. ............................ 73/585; 600/559; 702/57
(58) Field of Classification Search .................. 73/585, 73/520; 600/559; 702/57; 381/58, 23.1, 381/312, 314, 323, 60
See application file for complete search history.

(56) References Cited

U.S. PATENT DOCUMENTS

| 3,392,241 A | 7/1968 | Weiss et al. |
| 3,745,674 A | 7/1973 | Thompson et al. |
| 3,793,485 A | 2/1974 | Feezor et al. ................. 73/585 |
| 3,808,354 A | 4/1974 | Feezor et al. ................. 73/585 |
| 3,809,811 A | 5/1974 | Delisle ......................... 73/585 |
| 3,905,131 A | 9/1975 | Feezor et al. ............... 434/221 |
| 3,974,335 A | 8/1976 | Blackledge .................. 73/585 |
| 3,977,394 A | 8/1976 | Jones et al. ................. 600/541 |
| 4,022,975 A | 5/1977 | Krass ........................... 73/585 |
| 4,024,499 A | 5/1977 | Bosscher .................... 340/462 |

(Continued)

FOREIGN PATENT DOCUMENTS

JP  6-175817  6/1994

(Continued)

OTHER PUBLICATIONS

RION AA-75 Audiometer Operation Manual, RION Co, Ltd., Tokyo, Japan, No. 22920 Oct. 1995, pp. 130-132.*

(Continued)

*Primary Examiner*—John E. Chapman
(74) *Attorney, Agent, or Firm*—Kinney & Lange, P.A.

(57) ABSTRACT

A system and method for obtaining hearing ability related data from a subject outputs tones or sounds and monitors the subject's responses to the tones or sounds. An error condition is detected based on the responses, and corrective instructions are automatically delivered based on the error condition detected. The hearing evaluation is resumed by outputting tones or sounds, and the steps of outputting, monitoring, detecting, automatically delivering and resuming are iterated until evaluation of the subject's hearing has been completed.

16 Claims, 8 Drawing Sheets

U.S. PATENT DOCUMENTS

| | | | | |
|---|---|---|---|---|
| 4,038,496 | A | 7/1977 | Feezer | 73/585 |
| 4,107,465 | A | 8/1978 | Charlebois et al. | 73/585 |
| 4,157,456 | A | 6/1979 | Voss | 73/585 |
| 4,224,468 | A | 9/1980 | Calder, Jr. | 73/585 |
| 4,275,744 | A * | 6/1981 | Thornton et al. | 600/544 |
| 4,284,847 | A | 8/1981 | Besserman | 73/585 |
| 4,321,427 | A | 3/1982 | Singh | 73/585 |
| 4,476,724 | A | 10/1984 | Gotze | 73/585 |
| 4,489,610 | A | 12/1984 | Slavin | 73/585 |
| 4,548,082 | A | 10/1985 | Engebretson et al. | 73/585 |
| 4,615,007 | A | 9/1986 | King et al. | 600/559 |
| 4,667,683 | A | 5/1987 | Dugot | 600/559 |
| 4,731,850 | A | 3/1988 | Levitt et al. | 381/317 |
| 4,764,957 | A | 8/1988 | Angelini et al. | 379/433.06 |
| 4,768,165 | A | 8/1988 | Hohn | 73/585 |
| 4,847,763 | A | 7/1989 | Moser et al. | 600/559 |
| 4,862,505 | A | 8/1989 | Keith et al. | |
| 4,964,304 | A | 10/1990 | Eckstein | 73/585 |
| 5,023,783 | A | 6/1991 | Cohen et al. | 600/559 |
| 5,111,506 | A | 5/1992 | Charpentier et al. | 381/320 |
| 5,119,826 | A | 6/1992 | Baart de la Faille | 600/559 |
| 5,197,332 | A | 3/1993 | Shennib | 73/585 |
| 5,239,872 | A | 8/1993 | Meyer-Bisch | 73/585 |
| 5,282,475 | A | 2/1994 | Urbach et al. | 600/544 |
| 5,303,327 | A | 4/1994 | Sturner et al. | |
| 5,363,859 | A | 11/1994 | Tuckett et al. | 600/552 |
| RE34,961 | E | 6/1995 | Widin et al. | 703/6 |
| 5,428,998 | A | 7/1995 | Downs | 73/585 |
| 5,511,982 | A | 4/1996 | Pigache et al. | 434/350 |
| 5,525,977 | A | 6/1996 | Suman | 340/825.25 |
| 5,562,104 | A | 10/1996 | Hochberg et al. | 600/595 |
| 5,645,074 | A | 7/1997 | Shennib et al. | 600/559 |
| 5,737,389 | A | 4/1998 | Allen | 379/1.01 |
| 5,811,681 | A | 9/1998 | Braun et al. | 73/585 |
| 6,118,877 | A | 9/2000 | Lindemann et al. | 381/60 |
| 6,366,863 | B1 | 4/2002 | Bye et al. | 702/57 |
| 6,416,482 | B1 | 7/2002 | Braun et al. | 600/559 |
| 6,496,585 | B1 * | 12/2002 | Margolis | 381/60 |
| 6,644,120 | B1 * | 11/2003 | Braun et al. | 73/585 |

FOREIGN PATENT DOCUMENTS

| | | |
|---|---|---|
| JP | 7-308310 | 11/1995 |
| JP | 07308310 A * | 11/1995 |

OTHER PUBLICATIONS

Theresa Bedal, "Computerized Audiometry Helps Simplify Hearing Conservation Programs", *Safety & Health*, Jul. 1990, pp. 48-50.

June Antablin McCullough et al., "A Multimedia Approach for Estimating Speech Recognition of Multilingual Clients", *Clinical Focus, American Speech Language Hearing Association*, Oct. 28, 1993.

Tremetrics, "RA250 Automatic/Manual Screening Audiometer", 1993.

Theresa Y. Schulz, B.S., M.A., "Monitoring Audiometry in Hearing Conservation Programs", Dissertation, 1994.

Adnan Shennib, MS et al, "Personal Digital Audiometry: A New Dimension in Testing", *Hearing Instruments*, vol. 45, No. 3, 1994.

Tremetrics, "MATS 600 Group Audiometric Testing System", 1995.

Stephanie Zarrella, "Integrated Technology Enables Audiologists to Customize Computer Systems", *Advance for Speech-Language Pathologists & Audiologists*, Aug. 7, 1995.

"Decibel News", *The Official Newsletter of Decibel Instruments, Inc.*, Fall 1995.

Decibel, "Introducing Clinical Audiometry for Windows from Decibel Instruments, Inc," 1995.

Decibel, "Introducing Game Audiometry for Windows from Decibel Instruments, Inc," 1995.

Decibel, "Introducing the ProDigit 2000 Personal Digital Audiometer for Hearing Health Care Professionals from Decibel Instruments, Inc," 1995.

Decibel, "Introducing Screening Audiometry for Windows from Decibel Instruments, Inc," 1995.

Decibel, "Introducing Speech Perception for Windows from Decibel Instruments, Inc," 1995.

Decibel, "Introducing Word Identification Audiometry for Windows from Decibel Instruments, Inc," 1995.

RION Co. Ltd., *AA-75 Audiometer Operation Manual*, Excerpt from: Operation Manual, 10 pages (including English translation), Japan.

Virtual Corporation, *Virtual Model 320 Clinical Audiometer User Manual*, 1988, 148 pages.

Benson Medical Instruments Company, *Computer Controlled Audiometer (Model CCA100)*, Document Version #1.30, Dec. 13, 1994, 45 pages.

Benson Medical Instruments Company, *Computer Controlled Audiometer (Model CCA100)*, Document Version #1.20, Nov. 15, 1993, 14 pages.

Benson Medical Instruments Company, *CCA-100 Operating Manual*, V. 1.10, 1996, 51 pages.

Benson Medical Instruments Company, *System 100 Operating Manual*, V. 0.96, 1995, 48 pages.

Maico, *Service Manual MA728 and MA728M*, 56 pages, undated.

Maico, *Operating Instructions Maico MA728M Automatic Computer Audiometer—with Maico Warranty Registration*, 30 pages, undated.

Tremetrics Medical Instruments, *Sales Meeting, Technical Data and Troubleshooting*, Nov. 1990, 35 pages.

Tracor Instruments Austin, Inc. *RA600 Microprocessor Group Audiometer*, Service Manual, Jun. 1985, 37 pages.

* cited by examiner

MULTIMEDIA FEATURE FOR DIAGNOSTIC INSTRUMENTATION

CROSS-REFERENCE TO RELATED APPLICATION(S)

This application is a continuation of Ser. No. 10/156,415, filed May 28, 2002, now U.S. Pat. No. 6,644,120 B1 which is a division of application Ser. No. 09/139,858, filed Aug. 25, 1998, now U.S. Pat. No. 6,416,482, which is a continuation of application Ser. No. 08/639,694, filed Apr. 29, 1996, now U.S. Pat. No. 5,811,681.

BACKGROUND OF THE INVENTION

The present invention relates to a multimedia interface of a diagnostic test instrument and, more particularly, to automated testing, including multimedia-derived instructions, test monitoring, and error response, by an audiometer or other medical or diagnostic test instrument.

A wide variety of medical and diagnostic test instrumentation is known. An example of such instrumentation is an audiometer. The audiometer is an electrically activated generator of test tones for evaluation of hearing. Other medical and diagnostic instrumentations include a spirometer for measuring lung capacity, vision testing equipment, blood alcohol testing equipment, and occupational health industry maintenance testing equipment, such as blood pressure, EKG, and other wellness testing equipment. Generally, these and other prior testing instrumentations require one or more individuals to administer the test by operating the equipment and giving instructions to the test subject.

The trend in testing, however, appears to be toward automation. Through automation, reduced numbers of test administrators may be required and increased accuracy of testing, with lack of deviation caused by human administrator error, may be possible. Although certain limited automation has previously been possible, that automation has been directed primarily to the automated compilation, organization, and reporting of data in desirable formats. Processing units, such as, for example, personal computers, have previously been employed to achieve the automation of the compilation, organization, and reporting functions. Little automation, if any, has previously been achieved, however, in connection with the actual administration of the test. Administration of such tests has typically been performed almost wholly by one or more human test administrators.

Hearing testing has for several decades been performed utilizing an instrument called an audiometer. Prior to the audiometer, tuning forks and other tone generating devices were employed. In the early testing, a test subject responded directly to a test administrator who recorded test results based on the administrator's subjective determinations. The advent of the audiometer, an electronic instrument that generates tones, provided a degree of standardization in hearing testing because uniform tones and proper calibrations are better achieved.

Even after the invention of the audiometer, however, hearing testing was far from standardized, as testing varied in both procedures and determinations. A standardized procedure, still followed today, was then developed for hearing testing. That procedure is referred to as the "Hughson-Westlake" procedure. Other procedures are followed in some instances, but the Hughson-Westlake procedure is probably the most common.

In the Hughson-Westlake procedure, tones at a level audible to the test subject, such as, for example, 30 dB, are first presented to the subject. The test subject responds that the tones are heard, and then the level of the tones are reduced by 10 dB. This is repeated with the test subject responding that the tones are heard followed by 10 dB reductions until the test subject's response (or lack of response) indicates that the tones are not heard. When the test subject so responds that the tones are not heard, the tone level is raised 5 dB. If the test subject does not then respond, the level is raised another 5 dB, and this is repeated until the test subject signals that the tone is heard. This entire process is repeated until the test subject has three ascending positive responses at the same level. In order to make comparison of hearing quality over time, a first test is administered to establish a base line hearing level and later testing, undertaken at subsequent time intervals, provides results for comparison to base line. The comparison indicates any hearing loss or other changes over time.

As with diagnostic and industrial health testing instruments, generally, audiometers have progressed towards more automation. Also as with other instruments, however, automation of audiometers has typically focused on compilation, organization, and reporting of test results. The automation has not been directed to replacement of a human test administrator (or at least the traditional functions of such an administrator) by a machine automated process.

As previously mentioned, automation, particularly by a machine such as a computer, achieves certain advantages. In particular, the testing may be more uniform among subjects and test periods, whereas testing is subject to variation when a human test administrator administers and grades the test. Also, supplying human test administrators to conduct tests is rather costly. Reducing the required number of test administrators through further automation of testing procedures may reduce or eliminate those costs. Furthermore, test presentation and determined results may vary among human test administrators. More standardized and accurate testing may be possible if intervention of a human test administrator is reduced through further automation. In addition to those advantages, certain automation may provide added advantages, for example, multi-lingual test administration, multiple simultaneous different tests, multiple simultaneous test subjects, visual features, and other possibilities.

Embodiments of the present invention provide advantages of multimedia automation in diagnostic testing employing electronic or other instrumentation. The embodiments are particularly suited in the case of an audiometer, however, numerous other applications of the embodiments are possible. The above-described advantages, as well as other advantages, are achieved through the embodiments. The present invention is, thus, a significant improvement in the art and technology.

SUMMARY OF THE INVENTION

An embodiment of the invention is a method for automatedly administering an audiometric test. The method comprises the steps of controlling an audiometer to selectively switch the audiometer output between test tones generated by the audiometer and sound signals generated from digital information, first switching the audiometer output to sound signals when the step of controlling indicates a beginning of a new test, a completion of a current test, or a test error, outputting sound representative of the sound signals after the step of first switching, second switching the audiometer output to test tones after the step of outputting, and outputting test tones until the next step of first switching.

Another embodiment of the invention is a multimedia audiometer. The multimedia audiometer comprises means for outputting sound signals generated from digital information, means for outputting test tones, means for switching between the means for outputting sound signals and the means for outputting test tones, and means for controlling the means for switching, the means for controlling being communicatingly connected with the means for switching. The means for switching is communicatingly connected with the means for outputting sound signals and the means for outputting test tones.

Yet another embodiment of the invention is a multimedia audiometer. The multimedia audiometer comprises a computer, a tone generator, and a switch connected with the computer and the tone generator. The switch selectively causes either the tone generator or the computer to output sound waves, and the computer controls the switch.

Another embodiment of the invention is an audiometer. The audiometer comprises a processor, a memory, communicatingly connected with the processor, for storing digital data, a sound wave generator, for generating analog sound signals in respect of digital data, electrically connected with the processor, a test tone generator electrically connected with the processor, and a switch connected with the sound wave generator, the test tone generator, and the processor. The switch is controlled by the processor to selectively cause either the sound wave generator or the test tone generator to output sound waves.

A further embodiment of the invention is an instrument that conducts a test protocol on a test subject. The test protocol comprises an output by the instrument followed by an input to the instrument. The test subject determines the input, which input may be positive, negative, or null. The instrument comprises an output generator, an input detector for detecting the input, a digital data storage for storing a digital data, a multimedia converter, the multimedia converter converts the digital data to an analog signal, and logic circuitry connected to the input detector, the digital data storage, the multimedia converter, and the output generator, for logically operating on the input, reading the digital data, delivering the digital data to the multimedia converter, and controlling the output generator.

Yet another embodiment of the invention is a multimedia audiometer. The multimedia audiometer comprises a basic audiometer, a computer, a multimedia input interface communicatingly connecting the computer and the basic audiometer, and a communications interface communicatingly connecting the computer and the basic audiometer.

Another embodiment of the invention is a diagnostic instrument. The diagnostic instrument comprises means for outputting an audible sound, means for generating a test tone, means for storing a digital data, means for generating an analog signal derived from the digital data, means for switching an output of the means for outputting between the test tone and the analog signal, the means for switching being electrically connected to the means for generating a test tone and the means for generating an analog signal, means for processing, means for inputting, the means for inputting connects the means for processing to the means for outputting, and the means for communicating, the means for communicating connects the means for processing to the means for outputting, the means for generating the test tone, the means for storing the digital data, the means for generating the analog signal, the means for switching, and the means for inputting.

Yet another embodiment of the invention is a method of performing a diagnostic test protocol. The method comprises the steps of outputting an audible sound, generating a test tone, storing a digital data, generating an analog sound derived from the digital data, switching the audible sound from the step of outputting between the test tone and the analog signal, processing the digital data, and controlling the steps of outputting, generating the test tone, storing, generating the analog sound, and switching.

DETAILED DESCRIPTION

Figure 1:
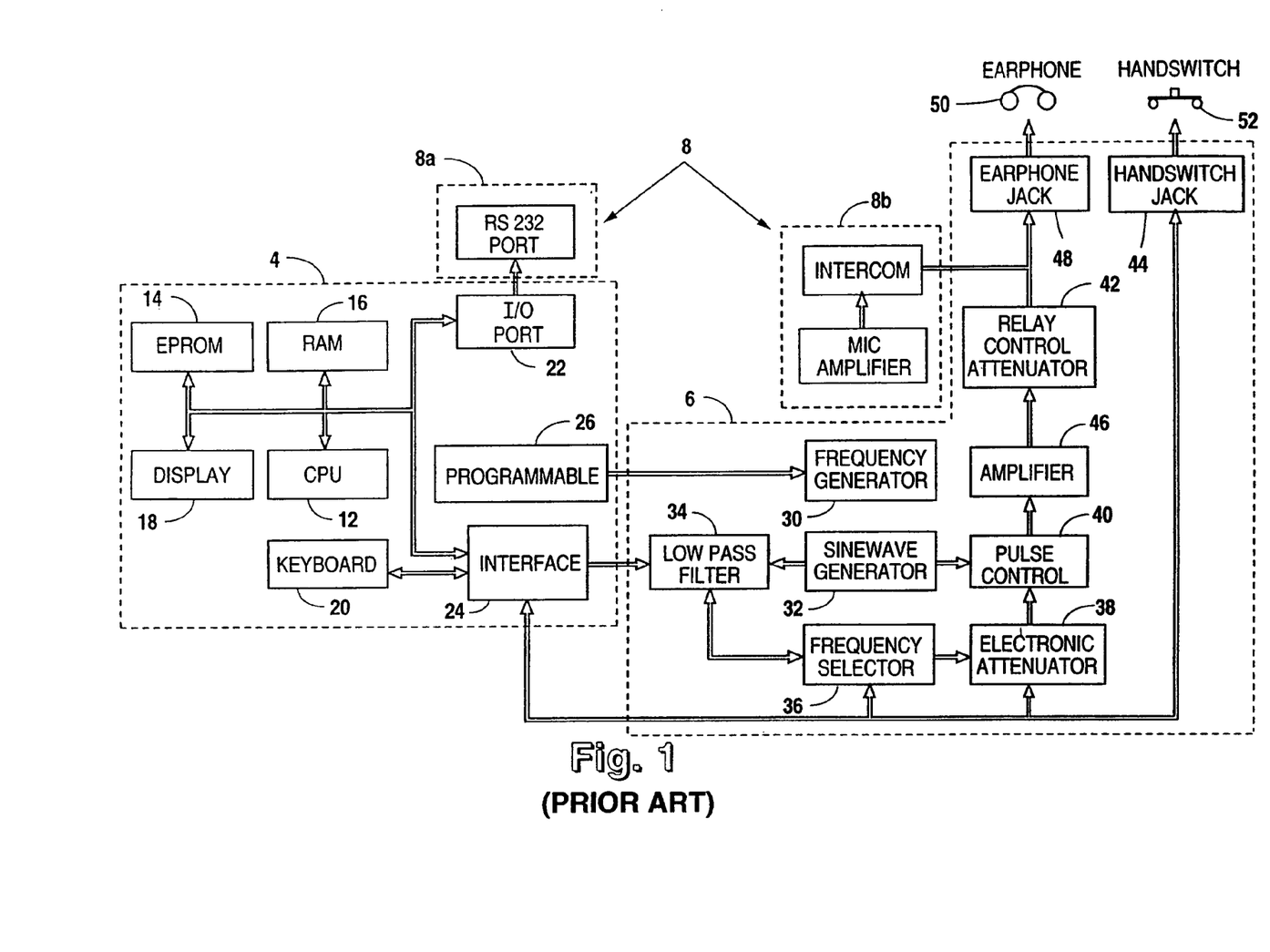
FIG. 1 is a functional block diagram of a conventional audiometer.

Referring to FIG. 1, a functional block diagram of a conventional audiometer 2 may be described. Although the following discussion primarily addresses embodiments of the present invention employed for an audiometer, the embodiments have varied application in a wide variety of medical and diagnostic instrumentation. All those applications are intended as included within the scope of the invention. Also, the following describes various embodiments of the present invention as particularly employed with the conventional audiometer 2. It is to be understood that the conventional audiometer 2 is detailed only for example purposes, and all other alternative audiometer configurations, as well as other instrumentation and configurations thereof, are also applications for the invention in accordance with the principles herein.

Conventional Audiometer

The conventional audiometer 2 is generally comprised of three parts: microprocessor circuitry 4, audio circuitry 6, and certain optional elements 8. In addition to those three parts, the conventional audiometer 2 includes a power supply and related elements not shown in the functional block diagram. One example of the conventional audiometer 2 is the RA250 Microprocessor Audiometer available from TREMETRICS, Inc., Austin, Tex. Of course, as previously mentioned, the conventional audiometer 2 illustrated is shown only for purposes of illustration and example. Other audiometers and other types of medical and diagnostic instrumentation are also within the scope of the invention.

Microprocessor Circuitry

The microprocessor circuitry 4 of the conventional audiometer 2 may include a processing unit (CPU) 12, such as, for example, an Intel™ 8085 microprocessor or another microprocessor. The CPU 12 serves to coordinate and control operations and functions of the conventional audiometer 2. The CPU 12 conductively connects with various memory, such as, for example, erasable programmable read only memory (EPROM) 14 and random access memory (RAM) 16. The memory 14, 16 may serve to store a software protocol which controls the CPU 12 to cause the conventional audiometer 2 to provide audiometric functions. The memory 14, 16 may also serve to maintain certain variables to achieve desired operations and calibration of the conventional audiometer 2, or simply to provide storage for values made available to and from the CPU 12.

In addition to the memory 14, 16, the CPU 12 conductively connects with various input and output ports and peripherals. Input and output ports may include a serial I/O port 22 and a parallel interface 24. The serial I/O port 22 may provide connections for certain optimal elements 8, as hereinafter discussed. The parallel interface 24 may connect with an input device, for example, a keyboard 20. The parallel interface 24 may also connect with the audio circuitry 6, as later explained. Another input device, such as a display 18, for example, may connect with the memory 14, 16, CPU 12, and other features of the microprocessor circuitry 4. Such other features of the microprocessor circuitry 4 may include, for example, certain programmable registers 26 and other elements.

Audio Circuitry

Now discussing the audio circuitry 6 of the conventional audiometer 2, the audio circuitry 6 interfaces with the microprocessor circuitry 4 in several ways. The programmable registers 26 may serve as ports that connect with an oscillator (also "frequency generator") 30. The oscillator 30 may provide timing for a sine wave generator 32 that produces a digitally synthesized sine wave from which audible test tones are derived. Because the sine wave generator 32 produces a digitally synthesized wave, the wave may be smoothed by a low pass filter 34.

The low pass filter 34 may connectively interface with the parallel interface 24 of the microprocessor circuitry 4. Other elements of the audio circuitry 6, such as frequency selector 36, an electronic attenuator 38, a pulse control 40, a relay control attenuator 42, and a handswitch jack 44, may conductively connect with the parallel interface 24 to complete the interface of the audio circuitry 6 with the microprocessor circuitry 4 of the conventional audiometer. Pursuant to this interface arrangement, the audio circuitry 6 and the microprocessor circuitry 4 may communicate signals for control and other purposes.

In addition to the connection of the low pass filter 34 with the parallel interface 24, the low pass filter 34 may conductively connect with frequency compensation circuitry, such as, for example, a frequency selector 36 that, together with the control provided through the parallel interface 24, helps compensate for attenuation. Other elements, such as the electronic attenuator 38 which connects with the frequency selector 36, also provide compensation for attenuation. The sine wine generator 32 feeds the pulse control 40 which, together with input to the pulse control 40 from the electronic attenuator 38, delivers signals representative of desired test tones to a power amplifier 46. The power amplifier 46 feeds the relay control attenuator 42 for left and right earphone signals. The relay control attenuator 42 is conductively connected with an earphone jack 48.

In order to allow a test subject to interface with the audio circuitry 6, earphone speakers 50 and a handswitch 52 may be provided. The earphone speakers 50 may plug into the earphone jack 48. The test subject wearing the earphone speakers 50 will then receive test tones generated by the conventional audiometer 2. The handswitch 52 may plug into the handswitch jack 44. The handswitch 52 provides means for the test subject to interface with the conventional audiometer 2 in order to signal to the conventional audiometer 2 that the test subject either does or does not correctly receive test tones through the earphone speakers 50.

Options

In addition to the basic elements just described, the conventional audiometer 2 may include certain optional elements 8. Various optional elements 8 are possible, depending upon desired operations and functions. Two common optional elements 8 of the conventional audiometer 2 have been an RS232 port 8a and a talkover card 8b. The RS232 port 8a may conductively connect to the serial I/O port 22 to allow communications of the microprocessor circuitry 4 with external peripherals (not shown) connected with the RS232 port 8a. Examples of external peripherals which may connect to the RS232 port 8a may include printers, terminals, and modems. The RS232 standard and suitable connections to ports conforming thereto are generally known.

The other of the common optional elements 8, the talkover card 8b, is of particular significance in embodiments of the present invention. The talkover card 8b is conductively connected with the audio circuitry 6 of the conventional audiometer 2 between the relay control attenuator 42 and the earphone jack 48. In effect, the talkover card 8b serves as a switch to divert input to the earphone jack 48 when desired by a human test administrator (not shown). The human test administrator may selectively "throw" the switch and cause the input to the earphone jack 48 to switch from signals from the relay control attenuator 42 representative of test tones to signals representative of the human test administrator's instructions then being voiced. Details of the talkover card 8b are hereinafter more fully discussed with respect to FIG. 3.

Figure 2A:
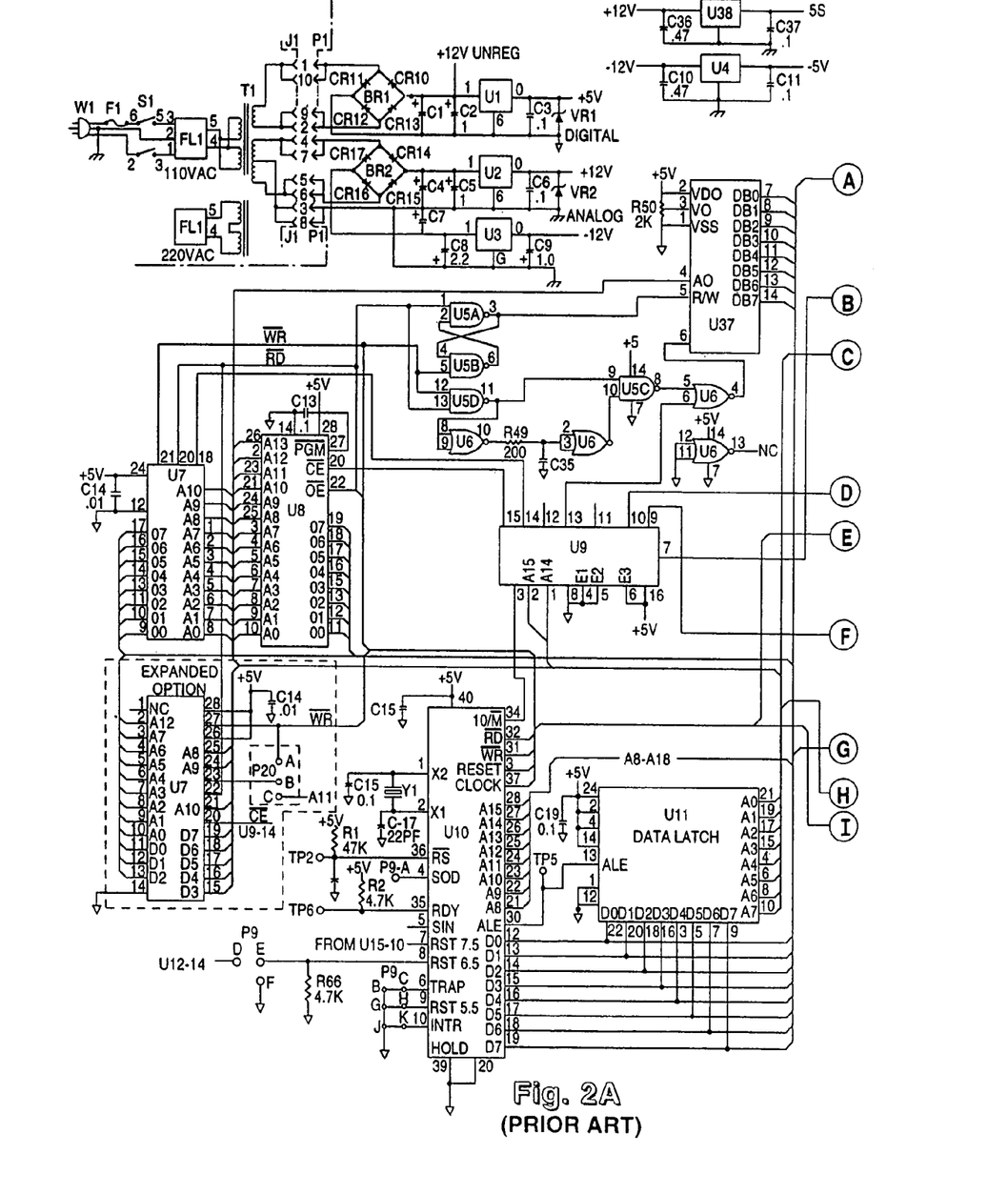
FIG. 2 is a detailed schematic of a typical audiometer, corresponding to the functional block diagram of FIG. 1.
Figure 2B:
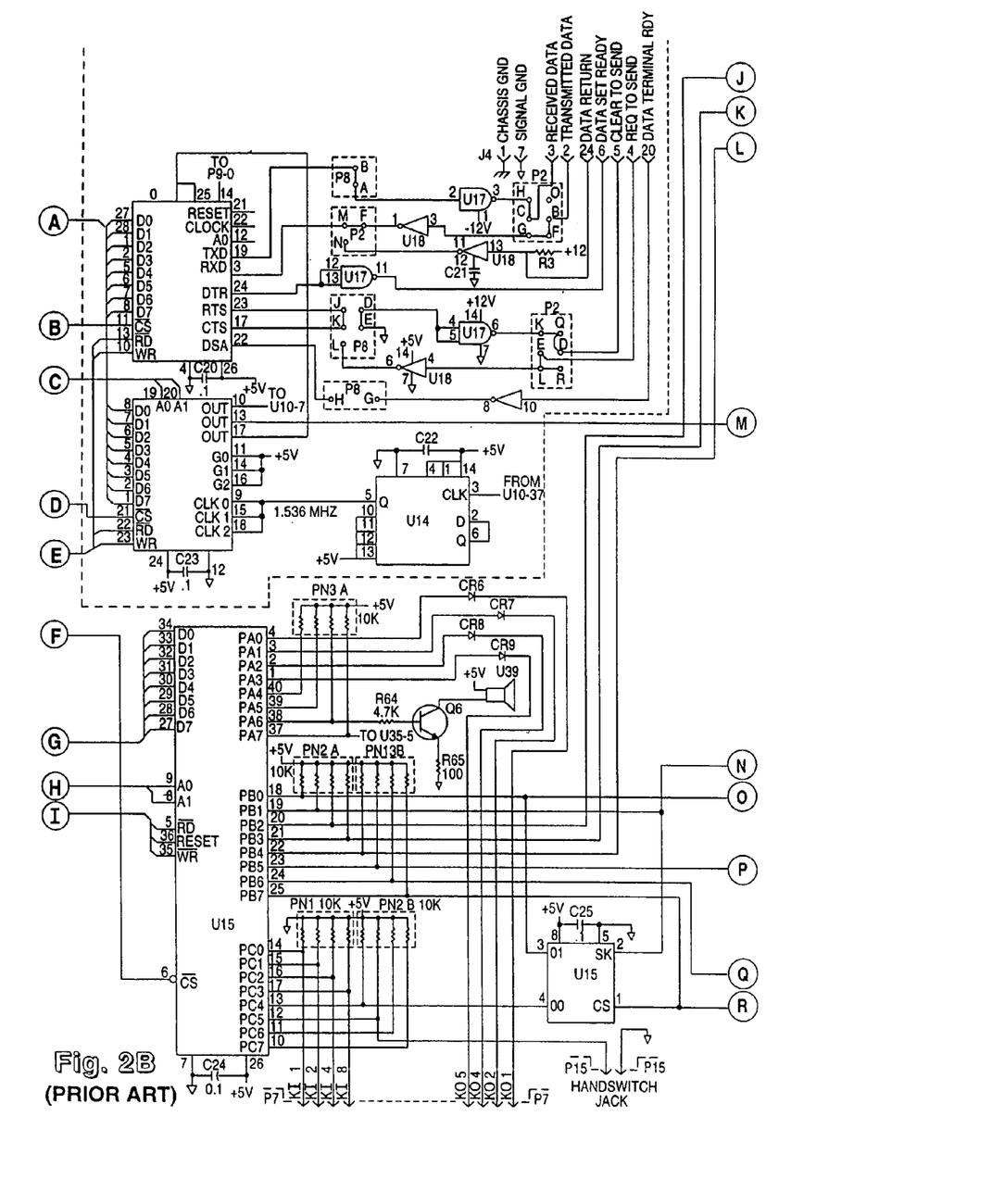
Figure 2C:
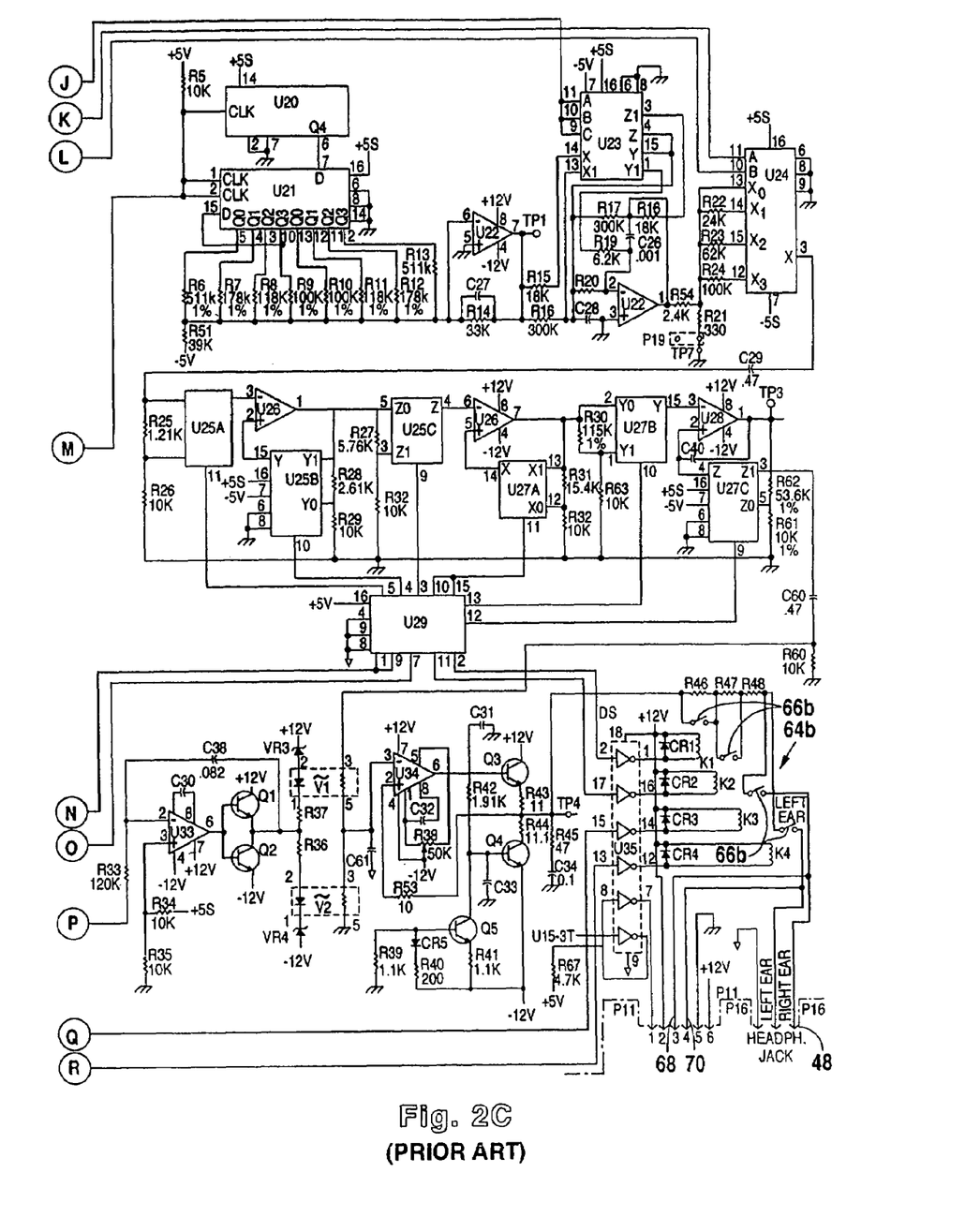

Referring now to FIG. 2, a detailed schematic of the conventional audiometer 2 of FIG. 1 is shown. Those skilled in the art will understand and appreciate the electrical elements and connectivities of the detailed schematic.

Figure 3:
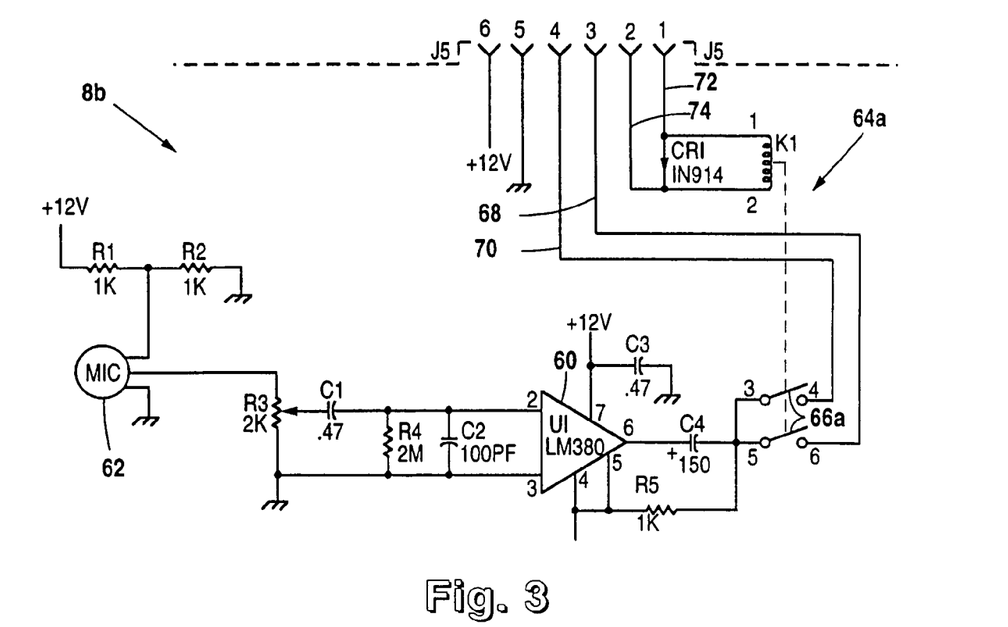
FIG. 3 is a schematic of a talkover card for use with the audiometer of FIG. 2.

Referring now to FIG. 3, a detailed schematic is provided of the talkover card 8b of the conventional audiometer 2. The talkover card 8b comprises a fixed gain operational amplifier 60. A voice microphone 62 is an input to the amplifier 60. Other common electronic elements, such as, for example, resistors, capacitors, and others, may be included in the circuitry of the talkover card 8b. The amplifier 60 is connected to the input to the earphone jack 48 of the audio circuitry 6 of the conventional audiometer 2 (shown in FIG. 1) by a relay 64a. When a human test administrator wishes to deliver voice sounds, rather than test tones, to a test subject wearing the earphone speakers 50 plugged into the earphone jack 48 (shown in FIG. 1), the test administrator causes the relay 64a to be thrown. The test administrator, by such action, simultaneously causes the conventional audiometer 2 to interrupt the test then in progress, discontinuing test tone generation.

Referring to FIGS. 1–3, in conjunction, the relay 64a when so thrown connects the amplifier 60, across switches 66a, to the input to the earphone jack 48. In particular, electrical connector 68 passes the voice signals from the amplifier 60 to the earphone jack 48 for delivery through the right ear speaker of the earphone speakers 50 and electrical connector 70 similarly passes the voice signals to the left ear speaker. When relay 64a results in closure of its switches 66a, relay 64b results in opening of its switches 66b, and vice versa. In this manner, either voice signals through the talkover card 8b or test tone signals through the audio circuitry 6 at any instant, but not both simultaneously, is delivered through the earphone speakers 50. As those skilled in the art will understand and appreciate, this design of the conventional audiometer 2 has allowed a human test administrator to interrupt test tone testing to give instructions, error messages, and other voice commands. The conventional audiometer 2 has required intervention of a human test administrator, however, by selectively throwing relays 64a,b and speaking into microphone 62 of the talkover card 8b, in order to conduct hearing test with intermittent instructions and messages.

Multimedia Embodiments

Figure 4:
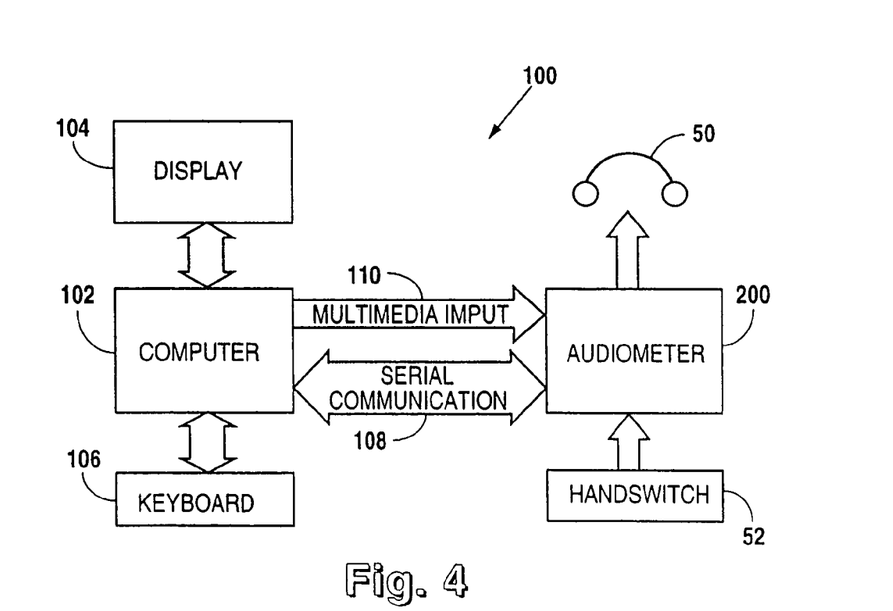
FIG. 4 is a block diagram of an audiometer interfaced with a personal computer for multimedia automation of audiometer testing.

Referring now to FIG. 4, a multimedia audiometer 100, according to embodiments of the present invention, may be described. The multimedia audiometer 100 includes a basic audiometer 200 having the basic elements of the conventional audiometer 2 (shown in FIG. 1). That is, the multimedia audiometer 100 is also comprised of the microprocessor circuitry 4 and the audio circuitry 6 (or other similar processing and audio electronics and circuits) of the conventional audiometer 2 (shown in FIG. 1). The earphone speakers 50 and the handswitch 52 are also interfaced with the basic audiometer 200.

Although the multimedia audiometer 100 and the conventional audiometer 2 share these similar basic elements, the basic audiometer 200 is merely a subset of the entire multimedia audiometer 100, as is apparent in FIG. 4. In addition to the elements of the basic audiometer 200, 2, the multimedia audiometer 100 includes a computer 102, such as a personal computer, another type of computer, or some other processing and storage device. The computer 102 may be equipped and connected with peripherals, such as a keyboard 106 and a display monitor 104, as well other known input/output, communications, printing, and peripheral equipment. In any event, the computer 102 should have multimedia capabilities, that is, the computer 102 should be capable of producing sound waves and/or visual images from representative digital information stored, generated, and/or manipulated within or by the computer 102.

The computer 102 may be conductively connected with the basic audiometer 200 through two interfaces: a communications interface 108 and a multimedia input interface 110. The communications interface 108 may allow for serial, parallel, or other communications. If communications are serial, the communications interface 108 may connect the computer 102 with the RS232 port 8a (shown in FIG. 1) in standard manner, as though the basic audiometer 200 is peripheral to the computer 102. The multimedia input interface 110 requires, however, that the conventional audiometer 2 be modified in certain respects to provide the basic audiometer 200 for multimedia automation of testing, as hereafter described.

Figure 5:
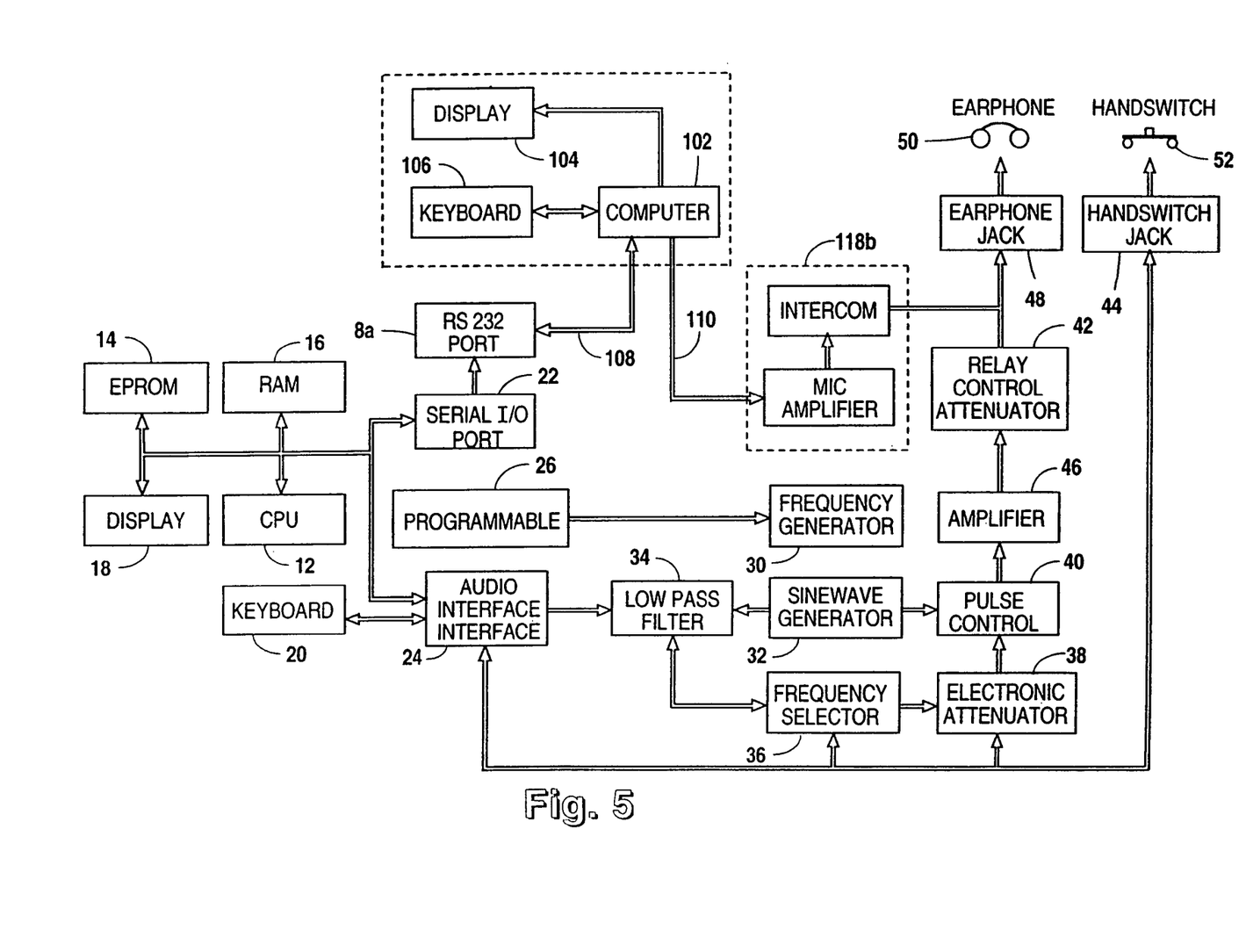
FIG. 5 is a functional block diagram of an audiometer interfaced with a multimedia personal computer.

Referring now to FIG. 5, the communications interface 108 and the multimedia input interface 110 connect the computer 102 with the basic audiometer 200 to form the multimedia audiometer 100, as shown in functional block form. A serial input/output port (not shown in detail) of the computer 102 may directly connect via the communications interface 108 with RS232 port 8a of the basic audiometer 200. A multimedia output port (not shown in detail) of the computer 102 may directly connect via the multimedia input interface 110 with a multimedia talkover card 118b, similar to the talkover cord 8b (shown in FIG. 3) of the conventional audiometer 2. The multimedia output port of the computer 102 may, for example, be a port of a sound card (not shown in detail) from which sound signals are output by the computer 102. Alternatively or additionally, other multimedia outputs (not shown) of the computer 102, for example, graphical image or video outputs, may connect with the multimedia input interface 110 in similar manner. The talkover card 8b (shown in FIG. 3) of the conventional audiometer 2 configuration has not previously provided a port for connection of the multimedia input interface 110. The conventional audiometer 2 may, therefore, be adapted to provide such port. The adapted conventional audiometer 2 is the basic audiometer 200.

Figure 6:
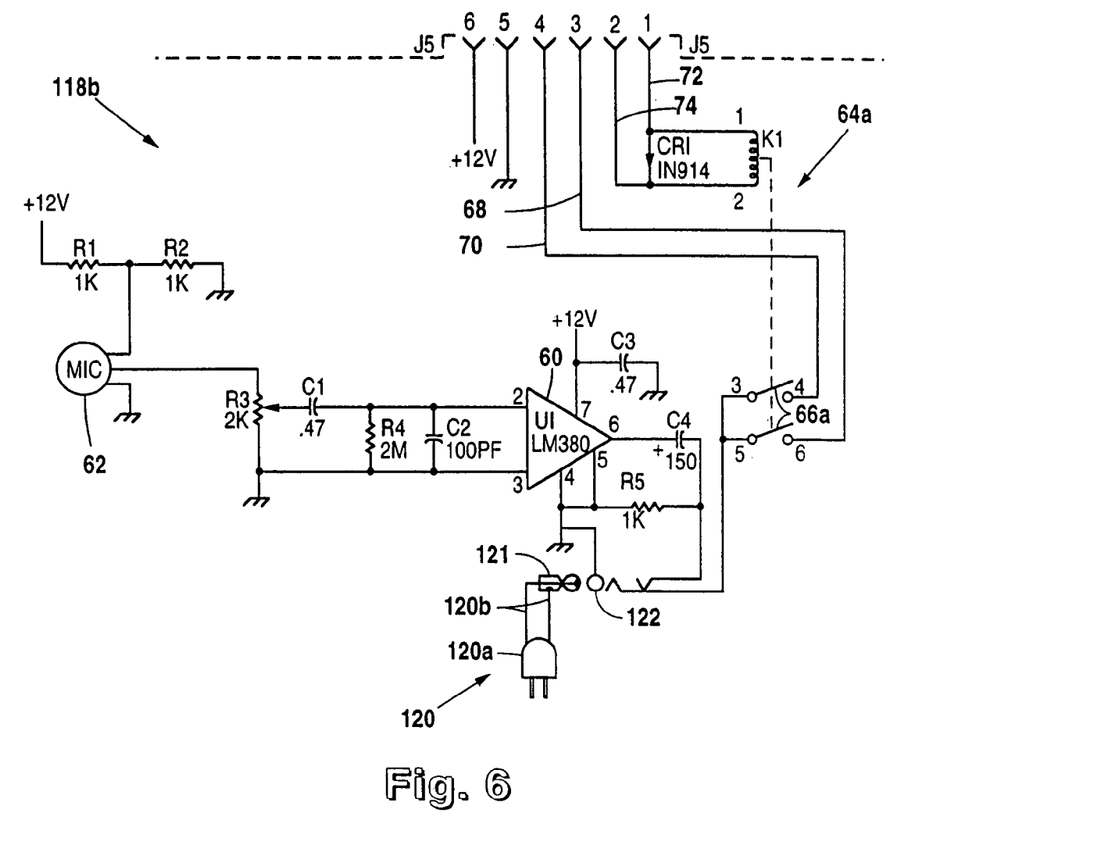
FIG. 6 is a schematic of the personal computer connection with the talkover card of FIG. 3, to provide multimedia automation of audiometer testing.

Referring now to FIG. 6, a sound port 120 of a multimedia talkover card 118b for multimedia input to the basic audiometer 200 may be described. The sound port 120 connects with the multimedia input interface 110, so that multimedia outputs of the computer 2 are input to the multimedia talkover card 118b. The sound port 120 may include a connector 120a to which the multimedia input interface 110 may be plugged. The connector 120a may be attached with two input leads 120b. The input leads 120a,b may be attached with an audio jack plug 121. The audio jack plug 121 is insertable in an audio jack 122 connected to the amplifier 60 output. When the audio jack plug 121 not is inserted in the audio jack 122, the output of amplifier 60 is shorted prior to the switches 66a. When the audio jack plug 121 is inserted in the audio jack 122, however, the circuit is completed and the computer 102 connected to the sound port 120 may supply multimedia input to the switches 66a. In effect, the microphone 62 is substituted with the multimedia input via the sound port 120. All other features of the multimedia talkover card 118b are substantially the same as the features of the talkover card 8b of the prior technology.

Although the input leads 120b of the sound port 120 are shown as connected with an output of the amplifier 60 in Figure, alternatively, the input leads 120b could in similar manner connect with inputs to the amplifier 60 or at some other location prior to or after the amplifier 60. Furthermore, although the multimedia talkover card 118b is expressly described as a "card" to the basic audiometer 200, it is to be understood that any other functional elements and circuitry that perform similarly, such as, for example, a relay circuit that switches between the tone generator of the basic audiometer 200 and the multimedia output from the computer 102, as well as other possibilities, are all within the scope of the invention.

Figure 7:
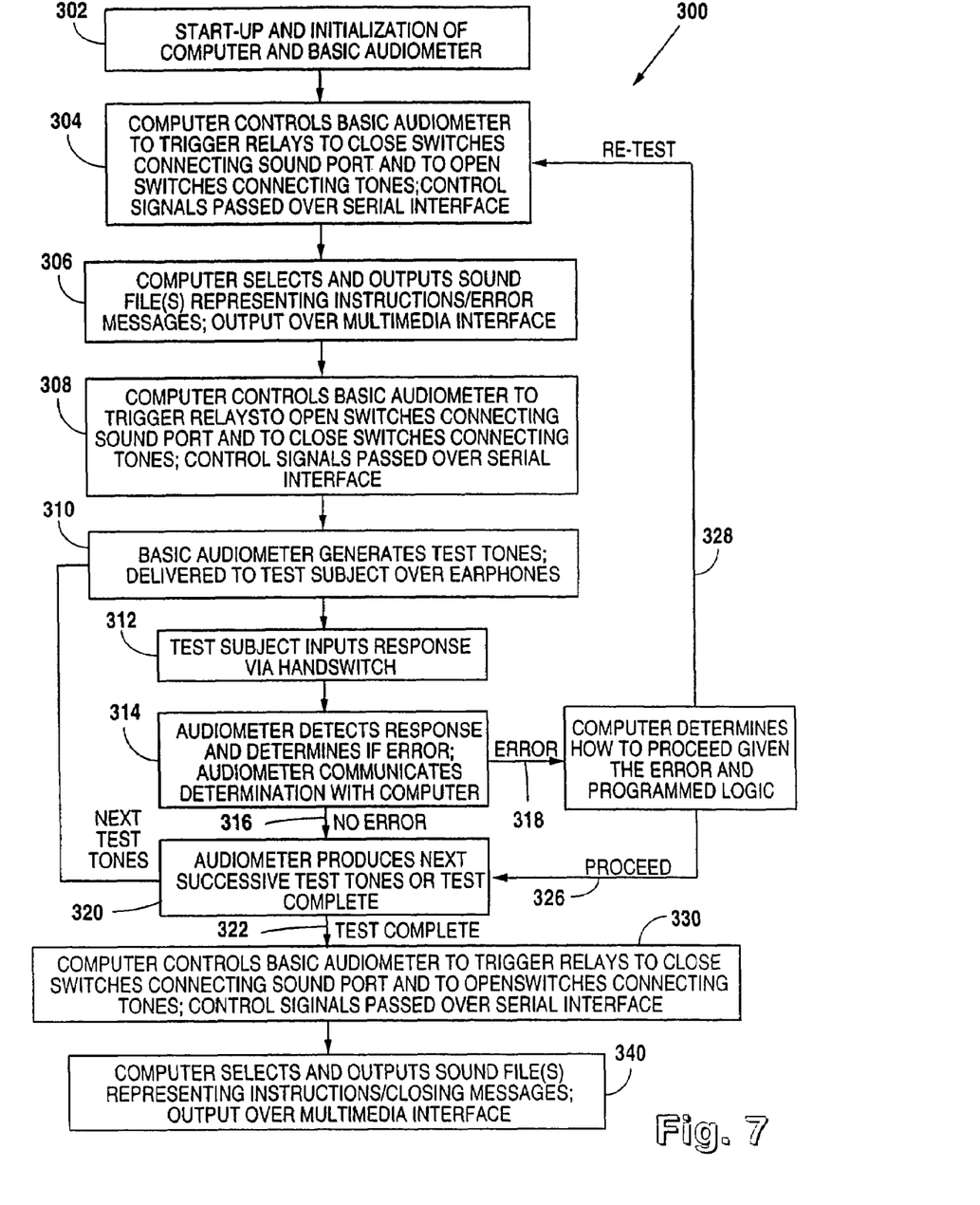
FIG. 7 is a flow diagram of a protocol for audiometric testing utilizing the multimedia features of the embodiments of the present invention to automate the test process.

Now referring to FIG. 7, in conjunction with FIGS. 4–6, operations 300 of the multimedia audiometer 100 and the software driving those operations 300 are discussed. When power is supplied to the multimedia audiometer 100, the basic audiometer 200, as well as the computer 102, may perform various set-up functions 302. Those set-up functions 302 of the multimedia audiometer 100, for example, boot-up and initialization of the computer 102 and start-up and initialization of the basic audiometer 200, are conventional. The start-up and initialization of the basic audiometer 200 may be substantially the same as that of the conventional audiometer 2 (shown in FIG. 1).

Generally, this start-up and initialization of the basic audiometer 200 may proceed, for example, as follows:

At turn-on, the basic audiometer 200 presents a first tone and a message appears on the display 18. The basic audiometer 200 is now ready for operation. If a processing error by the CPU 12 is discovered during the turn-on, an appropriate message is displayed.

The following example illustrates an initialization procedure for the basic audiometer 200. Keys of the keyboard 20 are indicated by [ ] and messages in quotes.

To begin, press:

| KEYBOARD | DISPLAY | COMMENT |
|---|---|---|
| [SPECIAL] | SPC00 | |
| [ENTER] | MM DD YY | |
| Now enter today's date. For example: | | |
| [04 30 96] | OM DD YY | |

The message "mode pulsed" then appears on the display 18. Press [NO] to switch to continuous mode. "Continuous Mode" will be displayed. Press [ENTER] when the desired code is displayed. The display should now read "1KL AA AUTO" and then displays "PRESS [NEW TEST]". Other parameters which may be selected include the test other ear first and delete 8000 Hz. To do this, press:

| KEYBOARD | DISPLAY | COMMENT |
|---|---|---|
| [SPECIAL] | SPC 04 | |
| [04] | SPC 04 | |
| [ENTER] | LEFT EAR FIRST | |
| [NO] | RIGHT EAR FIRST | |
| [ENTER] | 1KR AA AUTO | (Now testing right ear first) |
| [SPECIAL] | SPC 06 | |
| [06] | SPC 06 | |
| [ENTER] | 8KR SEL AUTO | |
| [NO] | 8KR DEL AUTO | |
| [ENTER] | 1KR AA AUTO | (8 Khz is deleted) |

The basic audiometer 200 is now initialized. Any or all of the above-mentioned parameters can be changed at any time by entering a desired special routine. Various "Special" codes that may be possible with the basic audiometer 200 of the multimedia audiometer 100 may, for example, include the following:

| SPECIAL | FUNCTION |
|---|---|
| 00 | Initialization of audiometer |
| 01 | Enter date and time |
| 02 | Mode Pulsed/Continuous |
| 03 | Enter Examiner ID |
| 04 | Invent runtable to test better ear first |
| 05 | Select Printer Format |
| 06 | Select or Delete 8K |
| 07 | Select Baud rate |
| 08 | Turn-on or off audio feedback for key pushes |
| 09 | Accelerated listening check |
| 10 | Check calibration date |
| 11 | Call Ram Rock check |
| 12 | Calibration mode and program calibration eeprom |
| 13 | Printer Text |
| 14 | Not used |
| 15 | Display routine for time and date (no entry) |
| 16 | Not used |
| 17 | Display selected audiogram |
| 18 | Print selected audiogram or audiograms |
| 19 | Display and/or enter serial number |
| 20 | Not used |

Software protocols to accomplish the start-up and initialization of the basic audiometer 200 may be stored in the memory 14, 16 of the basic audiometer 200 or elsewhere. Processing and control for the start-up and initialization of the set-up functions 302 are performed by the CPU 12 of the basic audiometer 200. Alternatively, the basic audiometer 200 could be controlled by the computer 102 to perform the start-up and initialization, or start-up and initialization could be controlled manually or in some other manner.

After the set-up functions 302, including start-up and initialization of the basic audiometer 200, are completed, the basic audiometer 200 may be ready to begin administering a new audiometric test of a test subject. A new test may be begun, for example, by pressing a key of the basic audiometer 200 or, alternatively, by a similar input to the computer 102. Upon the start of the new test, the computer 102 may control the basic audiometer 200 by communications over the communications interface 108 (shown in FIGS. 4–5).

If initial instructions to the test subject are desired, the computer 102 may control 304 the basic audiometer 200 over the communications interface 108 (shown in FIGS. 4–5). This control 304 may trigger the relay 64a and the relays 64b (shown in FIG. 2) to close the switches 66a and open the switches 66b (shown in FIG. 2), respectively. When the switches 66a are closed and the switches 66b are opened in this manner, sound signals passed to the sound port 120 from the computer 102 over the multimedia input interface 110 are delivered through the amplifier 69 of the multimedia talkover card 118b and through the earphone jack 48 to the earphone speakers 50.

The particular sound signals so passed to the earphone speakers 50 may be derived from digital information stored or generated in, or read by, the computer 102. The computer 102 may select and output 306 signals representative of the particular digital information. If the testing is just beginning, the signals so selected and output 306 may be initial instructions to the test subject about the test and the testing procedure. Of course, the particular signals could be representative of virtually any type of information which is subject to derivation from digital data. Although sound is described here as being derived from digital data, those skilled in the art will know and appreciate that digital data may be manipulated and processed in a multitude of ways to derive other types of information, for example, visual graphics and images and others.

After the computer has selected and output 306 the desired sound signals to the basic audiometer 200 and signals have been delivered to the test subject as sound waves through the earphone speakers 50, the computer 102, again may control 308 the basic audiometer 200. The control 308 at this instant may trigger the relay 64a to close the switches 66a and the relays 66b (shown in FIG. 2) to open the switches 66b, respectively. The control 308, then, causes the basic audiometer 200 to generate 310 a series of test tones, such as, for example, tones in accordance with the Hughson-Westlake procedure or another testing protocol.

When the switches 66a are closed and the switches 66b are opened because of the control 308, the test tones generated 310 by the audio circuitry 6 of the basic audiometer 200 are delivered through the earphone jack 48 to the earphone speakers 50. According to the particular testing protocol, the test subject may respond to the test tones by input 312 via the handswitch 52 connected to the basic audiometer 200. The basic audiometer 200, in cooperation with the computer 102, will detect and determine any error 314 of the input 312 response.

If there is not any error 316, then the basic audiometer 200 may continue to generate successive test tones 320 according to the particular test protocol, until the test is completed 322. The successive test tones 320 are generated in the same manner as previously described. That is, the basic audiometer 200 operates to generate test tones 310 delivered to the test subject; the test subject responds with input 312 via the handswitch 52; and the audiometer 200, in conjunction with the computer 102, detects and determines 314 any error.

If an error 318 is detected and determined 314, the computer 102, based on its particular programmed logic, determines 324 whether to proceed 326 with the testing, to re-test 328, or to perform some other function (not shown). Certain errors that may be encountered during the administration of the test include, for example, the following:

No response at 1 kHz, Error Code E1, signifies that the test subject is not responding to the test tone. The test subject may receive a multimedia sound message, generated by the computer 102 and passed through the earphone speakers 50, as to how to take the test, for example, as follows:

"There has been no response for any tone in the initial test—as soon as you hear a tone cut it off by pressing and releasing the hand switch."

Then, the test may be restarted.

Failed to Establish Threshold, Error Code E2, signifies that the basic audiometer 200 is unable to establish a hearing threshold level (HTL) from the response of the test subject. The test subject may be instructed based on digital data of the computer 102, for example, as follows:

"The audiometer has been unable to establish a threshold—listen for the tone and as soon as you hear the tone cut it off by pressing and releasing the hand switch."

The test may then recommence.

Hand Switch Error, Error Code E4, signifies that the test subject is not releasing the response handswitch 52. The test subject may, for example, receive the following instructions generated from the digital data stored by computer 102:

"The audiometer is recognizing the hand switch as being on for a length of time—as soon as you hear a tone cut it off by pressing and releasing the hand switch."

The test may then recommence.

Response no tone, Error Code E5, signifies that the test subject has responded at least three times when no tone or stimulus was present. A multimedia message, for example, as follows, may be delivered through the earphone speakers 50:

"The audiometer is recognizing responses when no tone is present—as soon as you hear a tone cut it off by pressing and releasing the hand switch."

The test is, thereafter, restarted.

The foregoing error codes, multimedia messages, and operations are merely example possibilities. An example of an entire error code list is as follows:

| Error Code | Indication | Multimedia Audiometer Response |
|---|---|---|
| AA | Not Tested | |
| DD | Deleted Frequency | |
| EE | No Response | Test Continues |
| EF | Test Incomplete | |
| EB | 25 Presentations No HTL | Test Continues |
| E1 | No Response 1 KHz | Stops Test Repeat Instructions |

-continued

| Error Code | Indication | Multimedia Audiometer Response |
|---|---|---|
| E2 | 1 KHz 25 Presentations No HTL | Stops Test Repeat Instructions |
| E3 | 1 KHz Retest Error | Stops Test Repeat Instructions |
| E4 | Hand Switch Error | Stops Test Holding Switch MSG |
| E5 | Response No Tone | Stops Test Response w/window closed |
| E6 | Error For Second Time | Stops Test Examiner Intervention |
| E7 | Max. Failed Frequencies >6 | Stops Test Examiner Intervention |
| E8 | Hardware Error | Only seen at Turnon and After EPROM Diagnostic Check |

Error Codes That Do Not Stop Test
EE
Error Codes that Get Instructions and Resume Testing
EB-Same as E2 message
E1
E2
E4
E5
Error Codes That Stop Test and Pop Up Message on PC for
Operator Test Does Not Restart
E3
E6
E7

In the case that a re-test 328 is warranted because of an error or otherwise, the operations 300 begin anew with the computer control 304 of the basic audiometer 200 over the communications interface 108 (shown in FIGS. 4–5) to trigger the relays 64a,b. The testing thereafter proceeds through the steps of selections and output 306, computer control 308, test tone generation 310, test subject response input 312, and detection and error determination 314.

Once the entire test protocol is completed in the foregoing manner, the test is completed 322. The computer 102 may then control 330 the basic audiometer 200 to trigger the relays 64a,b to close the switches 66a and to open the switches 66b. The control 330 is accomplished in the manners previously described by communications between the computer 102 and the basic audiometer 200 over the communications interface 108.

After the control 330 so sets the switches 66a,b, the computer 102 may further select and output 340 sound signals, which sound signals are derived from digital data stored, generated or read by the computer 102. The sound signals may travel to the earphone jack 48 and the earphone speakers 50 to deliver final instructions and messages to the test subject.

Numerous alternatives and variations are possible for the multimedia audiometer 100. For example, digital data stored, generated or read by the computer 102 may be representative of a wide variety of sounds, images, video, or other multimedia features. In certain embodiments, the particular digital data may allow the test subject to select any of a number of different languages through which testing is administered. Further, digital data may be manipulated by the computer 102 in such a manner that multiple simultaneous tests may be administered. There are, of course, numerous other possibilities.

There are also many possible variations and alternatives in the configuration of the computer 102 and the basic audiometer 200 by providing the audiometer with additional memory, processing, wave sound generation, and appropriate software. Alternatively, the computer 102 could include a test tone generation means and appropriate software programming to perform the functions of the basic audiometer 200. Even further, the multimedia audiometer 100 could be implemented by using a programmable digital tape player or compact disc (CD) player and allowing the basic audiometer 200 to select desired tracks to play. Other alternatives may be possible, it being understood that those skilled in the art will generally know and appreciate that the employment of computer or other control of instrumentation operations during test administration and the use of multimedia features for instruction, messages, and other herebefore required human administrative actions is possible with the incorporation of digital data, according to the embodiments of the present invention, from which are derived multimedia features.

It is to be understood that multiple variations, changes and modifications are possible in the aforementioned embodiments of the invention. Although illustrative embodiments of the invention have been shown and described, a wide range of modification, change, and substitution is contemplated in the foregoing disclosure and, in some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

Although the present invention has been described with reference to preferred embodiments, workers skilled in the art will recognize that changes may be made in form and detail without departing from the spirit and scope of the invention.

The invention claimed is:

1. A multimedia audiometer comprising:
   audio circuitry capable of generating audible test tones for delivery to earphones worn by a test subject;
   a computer selectively operable to produce instructions represented by sound waves for delivery to the earphones, the computer being operatively coupled to the audio circuitry;
   microprocessor circuitry operatively coupled to the computer, the microprocessor circuitry including a central processing unit (CPU) and a memory;
   an interface operatively coupled to the computer and the microprocessor circuitry for signaling whether the test subject perceives the audible test tones generated by the audio circuitry;
   a switch having a first state in which audible test tones generated by the audio circuitry are provided to the earphones, and a second state in which the instructions represented by sound waves produced by the computer are provided to the earphones; and
   software stored in at least one of the computer and the memory of the microprocessor circuitry, the software operating the computer, the microprocessor circuitry, the audio circuitry and the interface to generate the audible test tones for delivery to the earphones, monitor responses by the test subject, detect errors in the test subject's responses, selectively produce the instructions for delivery to the earphones in response to the detected errors, and to control the switch to switch to the second state when errors are detected in the test subject's responses and to automatically switch back to the first state following delivery of the instructions to the earphones so that testing is resumed without human intervention.

2. The multimedia audiometer of claim 1, wherein the responses of the test subject are compiled and stored in at least one of the computer and the memory of the microprocessor circuitry.

3. The multimedia audiometer of claim 2, wherein the software operates the computer, the microprocessor circuitry, the audio circuitry and the interface according to a pre-programmed logical testing procedure.

4. The multimedia audiometer of claim 3, wherein the logical testing procedure is the Hughson-Westlake procedure.

5. The multimedia audiometer of claim 1, wherein the software is stored in the computer.

6. The multimedia audiometer of claim 1, wherein the software is stored in the memory of the microprocessor circuitry.

7. The multimedia audiometer of claim 1, wherein the switch comprises a relay circuit.

8. A computer adapted to perform an audiometric test of a subject, comprising:
   a test tone generator operable to deliver audible test tones to earphones worn by the subject;
   an input/output interface; and
   software programmed to control the test tone generator to deliver the audible test tones to the earphones worn by the subject, monitor responses by the subject received over the input/output interface, detect errors in the subject's responses, selectively deliver audible corrective instructions to the earphones in response to the detected errors, and automatically resume delivery of the audible test tones after the audible corrective instructions are delivered without human intervention.

9. The computer of claim 8, wherein the software is operable to compile the responses of the subject and store results of the audiometric test.

10. The computer of claim 9, wherein the software is operable to display and/or print the results of the audiometric test.

11. A method of performing an audiometric test of a subject, comprising:
   controlling an audiometer to generate audible test tones in a headset worn by the subject;
   monitoring responses to the audible test tones by the subject;
   detecting errors in the subject's responses to the audible test tones;
   storing the detected errors in a computer memory;
   automatically producing selected audible corrective instructions in response to the detected errors and switching an input to the headset to the audible corrective instructions; and
   automatically switching the input to the headset back to the audible test tones after the audible corrective instructions are produced.

12. The method of claim 11, wherein the steps of controlling the audiometer to generate audible test tones and monitoring the subjects responses are performed according to a logical testing procedure.

13. The method of claim 12, wherein the logical testing procedure is the Hughson-Westlake procedure.

14. The method of claim 11, wherein the step of automatically producing selected audible corrective instructions in response to the detected errors and switching the input to the headset to audible corrective instructions, and the step of automatically switching the input to the headset back to the audible test tones after the audible corrective instructions are produced are performed by a computer.

15. The method of claim 11, further comprising:
displaying and/or printing results of the audiometric test.

16. The method of claim 11, further comprising:
halting the audiometric test when a threshold number of errors is determined.

* * * * *